United States Patent [19]

Sakai et al.

[11] Patent Number: 5,346,977
[45] Date of Patent: Sep. 13, 1994

[54] METHOD OF APPLYING A SKIN-PROTECTIVE COMPOSITION

[75] Inventors: Yoshio Sakai, Takefu; Izumi Saitoh, Nishinomiya, both of Japan

[73] Assignees: Shionogi & Co., Ltd., Osaka; Nissin Chemical Industry Co., Ltd., Fukui, both of Japan

[21] Appl. No.: 52,293

[22] Filed: Apr. 26, 1993

Related U.S. Application Data

[62] Division of Ser. No. 502,773, Apr. 2, 1990, abandoned.

[30] Foreign Application Priority Data

Apr. 1, 1989 [JP] Japan .................... 1-82549

[51] Int. Cl.⁵ .................... C08F 20/10; C08F 220/10
[52] U.S. Cl. .................... 526/318.44; 526/318.4; 523/105
[58] Field of Search .................... 523/105; 526/318.4, 526/318.44

[56] References Cited

U.S. PATENT DOCUMENTS

| | | | |
|---|---|---|---|
| 3,317,493 | 5/1967 | Selby | 526/318.44 |
| 3,927,203 | 12/1975 | Seymour et al. | |
| 3,980,602 | 9/1976 | Jakubauskas | 526/318.44 |
| 4,316,929 | 2/1982 | McIntire et al. | 526/318.44 |
| 4,673,571 | 6/1987 | Mahieu et al. | 526/318.44 |
| 4,874,830 | 10/1989 | Saitoh et al. | 526/318.4 |
| 5,229,435 | 7/1993 | Sakai et al. | 523/105 |

FOREIGN PATENT DOCUMENTS 0013836 8/1980 European Pat. Off. .
0265288 4/1988 European Pat. Off. .

*Primary Examiner*—Paul R. Michl
*Assistant Examiner*—LaVonda R. DeWitt
*Attorney, Agent, or Firm*—Wenderoth, Lind & Ponack

[57] ABSTRACT

A method of applying a skin-protective composition which comprises an acrylic copolymer which comprises (A) 40 to 85% by weight of an alkyl acrylate,
(B) 5 to 50% by weight of an alkyl methacrylate, and
(C) 10 to 30% by weight of a mono-ethylenically unsaturated monomer having a carboxyl group, and a medium, which can effectively block irritative materials and be easily removed from a skin.

9 Claims, 3 Drawing Sheets

METHOD OF APPLYING A SKIN-PROTECTIVE COMPOSITION

This application is a divisional of now abandoned application, Ser. No. 07/502,773, filed Apr. 2, 1990.

BACKGROUND OF THE INVENTION

1. Field of the Invention

The present invention relates to a skin-protective composition. In particular, the present invention relates to a skin-protective composition comprising an acrylic copolymer which is soluble in a general solvent such as an alcohol and a weakly alkaline aqueous solution, a film formed from which copolymer has good skin-protecting properties.

2. Description of the Related Art

There are known skin-protecting agents which protect human skin from chemicals or other irritative materials.

The protecting agent is applied to the skin by coating or spraying to form a film which protects the skin. However, the conventional protecting agents have drawbacks such that an organic solvent in the agents such as acetone or ethyl acetate irritates the skin or the formed film is not easily removed from the skin.

U.S. Pat. No. 4,874,830 and Japanese Patent Kokai Publication No. 104909/1988 discloses a skin-protecting agent for protecting the skin of persons who wash dishes or apparatus with neutral detergents at home or in restaurants, hospitals, beauty shops and the like, which agent comprises an ethyl acrylate-methacrylic acid copolymer and ethylcellulose. The proposed skin-protecting agent effectively blocks many irritative materials, although some low molecular weight irritative materials permeate through the film of the agent.

SUMMARY OF THE INVENTION

One object of the present invention is to provide a skin-protective composition not containing such an organic solvent as to stimulate the skin and effectively blocking irritative materials.

Another object of the present invention is to provide a skin-protective composition which forms an easily removable film.

These and other objects are achieved by a skin-protective composition which comprises an acrylic copolymer which comprises (A) 40 to 85% by weight of an alkyl acrylate,
(B) 5 to 50% by weight of an alkyl methacrylate, and
(C) 10 to 30% by weight of a mono-ethylenically unsaturated monomer having a carboxyl group, and a medium.

DETAILED DESCRIPTION OF THE INVENTION

Figure 1:
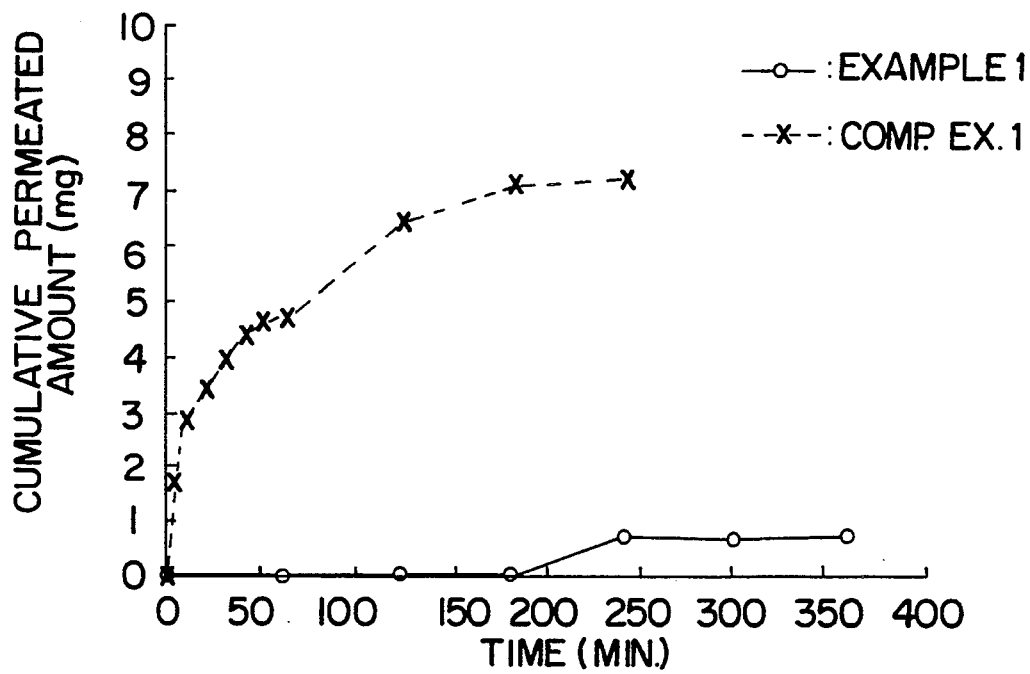
FIGS. 1 to 5 show the cumulative permeated amounts of the chemicals through the films formed from the copolymers of Examples and Comparative Examples.

Preferred example of the alkyl acrylate (A) is an alkyl acrylate having 1 to 6 carbon atoms in the alkyl group, in particular, ethyl acrylate, propyl acrylate or butyl acrylate.

Preferred example of the alkyl methacrylate (B) is an alkyl methacrylate having 1 to 6 carbon atoms in the alkyl group, in particular, methyl methacrylate or ethyl methacrylate.

The alkyl acrylate (A) and the alkyl methacrylate (B) impart the copolymer with solubility in a solvent, film formability, compatibility and adhesiveness to other materials such as the skin. Since the alkyl acrylate imparts flexibility to the copolymer film and the alkyl methacrylate imparts stiffness to the copolymer film, flexibility and stiffness of the copolymer film can be adjusted by varying the ratio of these two components.

The amount of the alkyl acrylate (A) is from 40 to 85% by weight, preferably from 55 to 75% by weight based on the total weight of the components (A), (B) and (C). When the amount of the alkyl acrylate (A) is less than 40% by weight, the film formed from the copolymer has insufficient flexibility. When said amount is larger than 85% by weight, the film becomes tacky and has insufficient strength.

The amount of the alkyl methacrylate (B) is from 5 to 50% by weight, preferably from 10 to 30% by weight based on the total weight of the components (A), (B) and (C). When this amount is less than 5% by weight, the film cannot sufficiently prevent the permeation of the irritative materials. When said amount is larger than 50% by weight, the formed film has insufficient flexibility.

Specific examples of the mono-ethylenically unsaturated monomer having the carboxyl group (C) are acrylic acid, methacrylic acid, crotonic acid, itaconic acid, maleic acid, fumaric acid, half-esters of maleic acid, half-esters of fumaric acid and the like. The monomer (C) improves the adhesivity of the copolymer film to the skin and reduces electrostatic charge. In addition, the monomer (C) imparts swellability with or dispersibility in a weak alkali such as an amine, aqueous ammonia or an aqueous solution of soap to the copolymer and makes it easy to remove the film from the skin. The amount of the monomer (C) is from 10 to 30% by weight, preferably from 10 to 20% by weight based on the total weight of the components (A), (B) and (C). When the amount of the monomer (C) is less than 10% by weight, it is not easy to remove the copolymer film from the skin. When said amount is larger than 30% by weight, the water resistance of the copolymer is deteriorated and the copolymer film loses flexibility.

The acrylic copolymer of the present invention may further comprise other monomer in addition to the above essential components. Examples of the other monomer are vinyl monomers such as vinyl acetate, 2-hydroxyethyl methacrylate and N-vinylpyrrolidone. The amount of the other monomer is preferably not larger than 20% by weight based on the total weight of the components (A), (B) and (C). Otherwise, the copolymer may no achieve the effects of the present invention.

The acrylic copolymer to be used in the present invention preferably has a glass transition temperature ($T_g$) of $-10°$ to $+50°$ C. When the glass transition temperature is lower than $-10°$ C., the formed film is soft, has decreased tensile strength and becomes tacky. When the glass transition temperature is higher than $+50°$ C., the film has poor elongation and gives stiff feeling to the skin.

The acrylic copolymer has a weight average molecular weight of 30,000 to 1,500,000, preferably 50,000 to 1,000,000 measured by the GPC method. When the molecular weight is less than 30,000, the tensile strength of the film decreases and its functionality is deteriorated. When the molecular weight is larger than 1,500,000, the skin-protective composition has increased viscosity so that spinnability occurs during application of the composition to the skin.

The acrylic copolymer of the present invention may be prepared by copolymerizing the above monomers by a per se conventional method. The polymerization mode may be solution polymerization or emulsion polymerization.

For example, the solution polymerization is carried out by heating the monomer mixture in a solvent in the presence of a polymerization initiator while stirring. Examples of the solvent are methanol, ethanol, isopropanol, acetone, methyl ethyl ketone, methyl acetate, ethyl acetate, ethyleneglycol monoalkyl ether and the like. Examples of the polymerization initiator are solvent-soluble ones such as dibenzoyl peroxide, cumene hydroperoxide, diisopropyl peroxydicarbonate and azobisisobutyronitrile.

The emulsion polymerization is carried out by heating a dispersion of an emulsifier, a water-soluble polymerization initiator and the monomer mixture in water while stirring. Preferred examples of the emulsifier are anionic or nonionic surfactants such as sodium laurylsulfate, sodium N-lauroylsarcosinate, polyoxyethylene lauryl ether, polyoxyethylenesorbitan monooleate, sorbitan sesquioleate, glyceryl monostearate, aliphatic acid esters with sucrose and the like. Examples of the water-soluble polymerization initiator are ammonium persulfate, potassium persulfate, hydrogen peroxide, tert.-butyl hydroperoxide and the like. Optionally, a reducing agent such as sodium hydrogensulfite and L-ascorbic acid can be used.

The solution or emulsion of the copolymer obtained from the polymerization process may be used as the skin-protective composition of the present invention. Preferably, to the solution of the copolymer, water, ethylene glycol or a hydrocarbon base no-solvent (e.g. n-hexane) is added to precipitate the copolymer from the solution. Then, the precipitated copolymer is washed with water or the non-solvent hydrocarbon, purified and dried. The emulsion of the copolymers is coagulated with the addition of an acid or an aqueous solution of a salt such as sodium sulfate and calcium chloride and the coagulated copolymer is washed with water, purified and dried. Then, to the dried copolymer, a suitable medium is added to prepare the skin-protective composition of the present invention.

The skin-protective composition of the present invention comprises the copolymer and a medium and can be in the form of a solution, a cream or a spraying liquid. The medium is preferably a solvent such as a lower alcohol or a solvent which is generally used in the preparation of a lotion, a cream or a spraying liquid. Preferred examples of the medium are ethanol, isopropanol and a mixture of water and ethanol or isopropanol.

Preferably, the skin-protective composition of the present invention is in the solution form. The concentration of the copolymer in the solution is from 1 to 30% by weight, preferably from 5 to 10% by weight. When the mixed solvent of water and an alcohol is used, a ratio of water to the alcohol can vary in a wide range.

To the skin-protective composition of the present invention, other resin may be added. For example, the addition of a cellulose derivative such as ethylcellulose or hydroxypropylcellulose will improve the film properties of the copolymer.

The film of the copolymer of the present invention effectively prevents permeation of irritative materials such as perillaldehyde, benzyl alcohol, sodium benzoate, benzalkonium chloride, chlorohexidine gluconate, and the like.

When a small amount of the skin-protective composition is applied to the skin, a very thin film of the copolymer is formed on the skin. The formed film has sufficient water resistance and acid resistance, has good elongation and flexibility, and well adheres to the skin without malaise. In addition, the copolymer is very safe to the skin since it has no or little irritation to the skin and well blocks the irritative materials.

The formed film can be easily and safely removed from the skin with a weakly alkaline aqueous solution such as an aqueous solution of soap or an alcohol such as ethanol.

PREFERRED EMBODIMENTS OF THE INVENTION

The present invention will be illustrated by following Examples, in which "parts" are by weight unless otherwise indicated.

EXAMPLE 1

In a closed reactor equipped with a stirrer, ethyl acetate (75 parts) was charged, an internal atmosphere was replaced with nitrogen gas and an internal temperature of the reactor was adjusted at 55° C. To the content of the reactor, diisopropyl peroxydicarbonate (0.5 part) was added. Then, a monomer mixture of methyl methacrylate (20 parts), ethyl acrylate (65 parts) and methacrylic acid (15 parts) and 0.5% solution of diisopropyl peroxydicarbonate in ethyl acetate (100 parts) were added over 4 hours while keeping the internal temperature of the reactor at 55° C. The content of the reactor was stirred at 55° C. for 2 hours and at 77° C. for 3 hours to complete polymerization, followed by cooling to room temperature to obtain a copolymer.

In a mixer, the reaction mixture was poured. To the mixture, n-hexane (1000 parts) was gradually added while stirring under shear to precipitate the purified copolymer, which was recovered by filtration, washed with n-hexane and dried. Yield of the copolymer was 94%. The copolymer had the glass transition temperature of 12.8° C. and the weight average molecular weight of $8.5 \times 10^4$ (by GPC).

The copolymer was dissolved in ethanol at a concentration of 30% to obtain a solution.

EXAMPLES 2–6

In the same manner as in Example 1 but using a monomer mixture shown in Table 1, a copolymer was prepared, and a 30% solution of the copolymer in ethanol was obtained. The monomeric composition and the properties of the copolymer are shown in Table.

TABLE

| | Example No. | | | | | |
|---|---|---|---|---|---|---|
| | 1 | 2 | 3 | 4 | 5 | 6 |
| MMA | 20.0 | 10.0 | 30.0 | 39.0 | — | 18.0 |
| EA | 65.0 | 75.0 | 55.0 | — | 60.0 | 62.0 |
| MAA | 15.0 | 15.0 | 15.0 | 15.0 | 15.0 | 15.0 |
| BA | — | — | — | 46.0 | — | — |
| EMA | — | — | — | — | 25.0 | — |
| 2-HEMA | — | — | — | — | — | 5.0 |
| $M_w (\times 10^4)$ | 8.5 | 18.6 | 7.6 | 9.1 | 10.3 | 7.9 |

TABLE-continued

| | Example No. | | | | | |
|---|---|---|---|---|---|---|
| | 1 | 2 | 3 | 4 | 5 | 6 |
| $T_g$ (°C.) | 12.8 | 2.0 | 24.4 | 12.6 | 12.0 | 12.8 |

Note:
MMA: Methyl methacrylate.
EA: Ethyl acrylate.
MAA: Methacrylic acid.
BA: Butyl acrylate.
EMA: Ethyl methacrylate.
2-HEMA: 2-Hydroxyethyl methacrylate.

EXAMPLE 7

In a closed reactor equipped with a stirrer, deionized water (67.0 parts), isopropanol (1.5 parts) and ferrous sulfate (0.0025 part) were charged, the internal atmosphere was replaced with nitrogen gas and the internal temperature was adjusted at 60° C.

A monomer mixture of methyl methacrylate (20.0 parts), ethyl acrylate (65.0 parts) and methacrylic acid (15.0 parts) was emulsified by means of a homogenizer in deionized water (100 parts) in the presence of sodium laurylsulfate (0.5 part) and Polysolvate 80 (polyoxyethylenesorbitan monooleate) (1.0 part) to prepare an emulsion.

Then, this emulsion, a 0.75% aqueous solution of ammonium persulfate (33.3 parts) and a 0.6% aqueous solution of sodium hydrogensulfite (33.3 parts) were separately dropwise added to the reactor kept at 60° C. over 4 hours. The reaction mixture was further stirred for 2 hours at 60° C. to complete the polymerization to obtain an emulsion of the copolymer.

To the resulting emulsion, dilute sulfuric acid was added to coagulate the copolymer, which was recovered by filtration, washed with water and dried. The copolymer had the glass transition temperature of 12.8° C. and the weight averaged molecular weight of $42.6 \times 10^4$.

The copolymer was dissolved in ethanol at a concentration of 30% to obtain a transparent solution.

EXAMPLE 8

In the same manner as in Example 1 but using a mixed solvent of ethanol and water in a weight ratio of 70:30 in place of ethanol, a 30% solution of the copolymer in the mixed solvent was obtained.

EXAMPLE 9

In the same manner as in Example 1 but using a monomer mixture of methyl methacrylate (25 parts), ethyl acrylate (65 parts) and acrylic acid (10 parts), a 30% solution of the copolymer was obtained.

EXAMPLE 10

In the same manner as in Example 1 but using a monomer mixture of methyl methacrylate (20 parts), ethyl acrylate (60 parts) and methacrylic acid (20 parts), a 30% solution of the copolymer was obtained.

EXPERIMENTS

With each of the solutions prepared in Examples 1-7 and the skin-protecting agent of Example 8 of U.S. Pat. No. 4,874,830 (corresponding to Example 1 of Japanese Patent Kokai Publication No. 104909/1988) (as Comparative Example 1), the following tests were carried out:

1. Film permeability

With a table coater (HIRANO KINZOKU CO., LTD.), a film of about 50 μm in thickness was formed from the solution. With the formed film, effect for preventing permeation of a chemical was evaluated in vitro.

In a Franz type cell having a permeation area of 10 cm², the film was attached with using a 0.45 μm membrane filter as a support. After filling purified water in a receptor part, a 1% aqueous solution of the chemical to be tested (1 ml) was charged in a donor cell. Then, an amount of the chemical which was permeated to the receptor cell through the film was measured as time passes and a cumulative permeated amount of the chemical was calculated. As model compounds for irritative materials having different molecular weights, benzyl alcohol, benzalkonium chloride and chlorohexidine gluconate were used.

Figure 2:
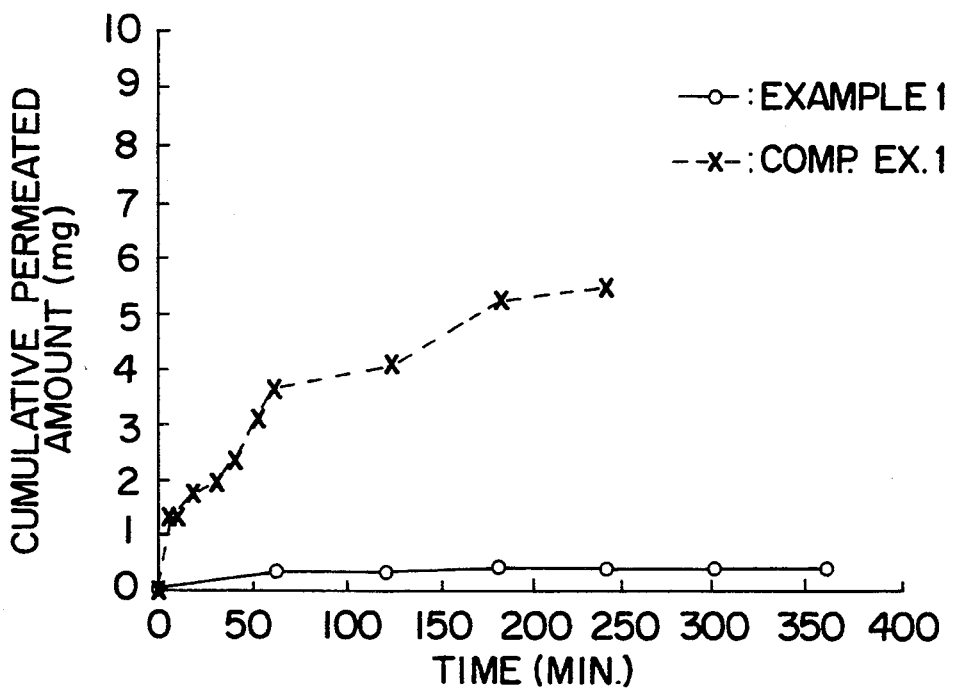
Figure 3:
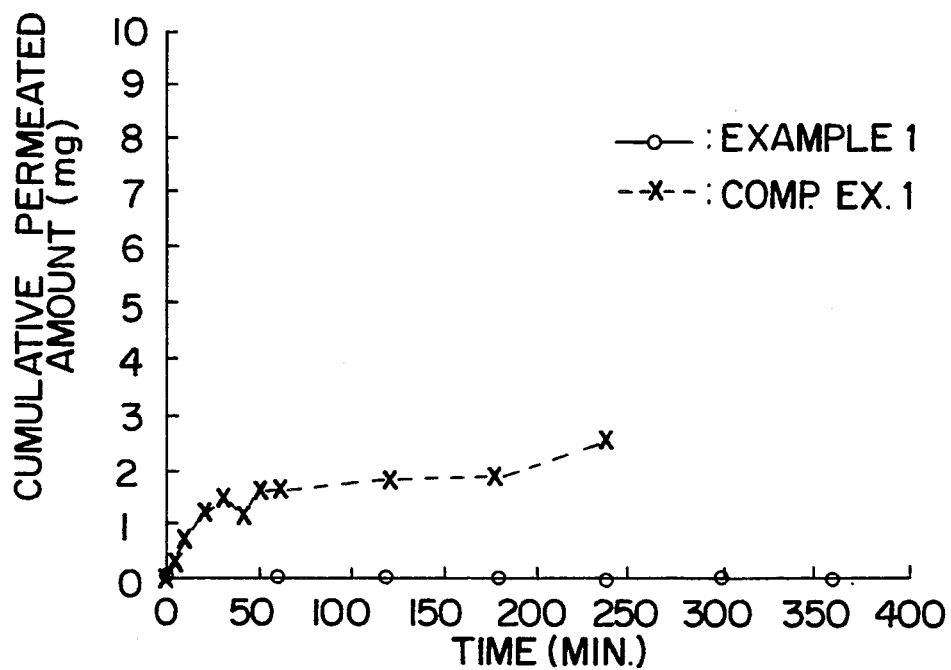
Figure 4:
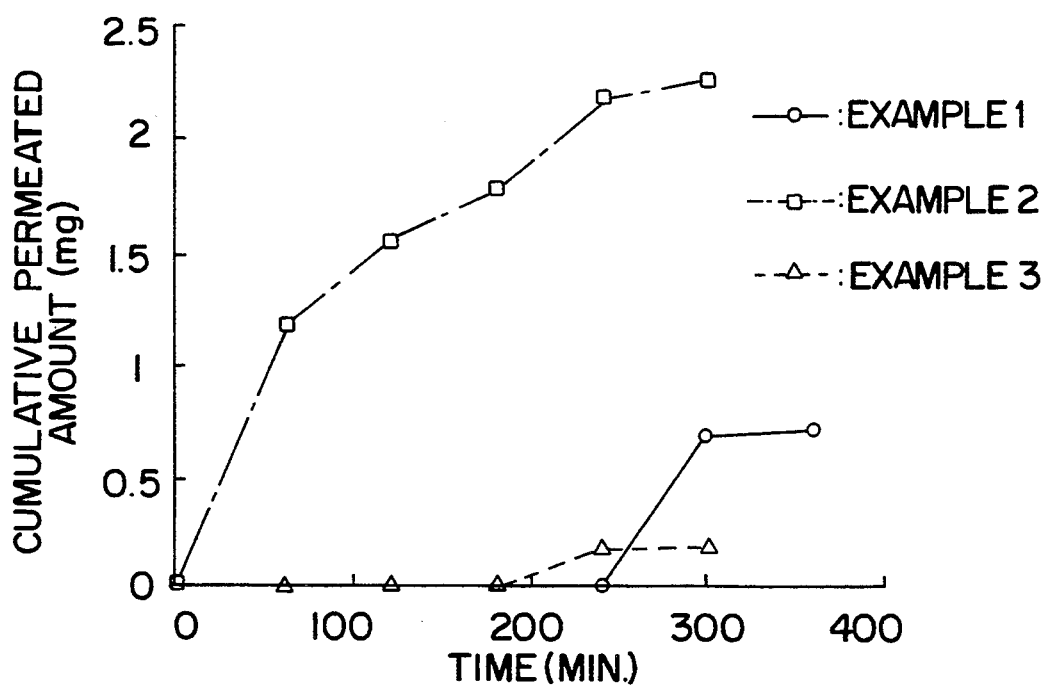
Figure 5:
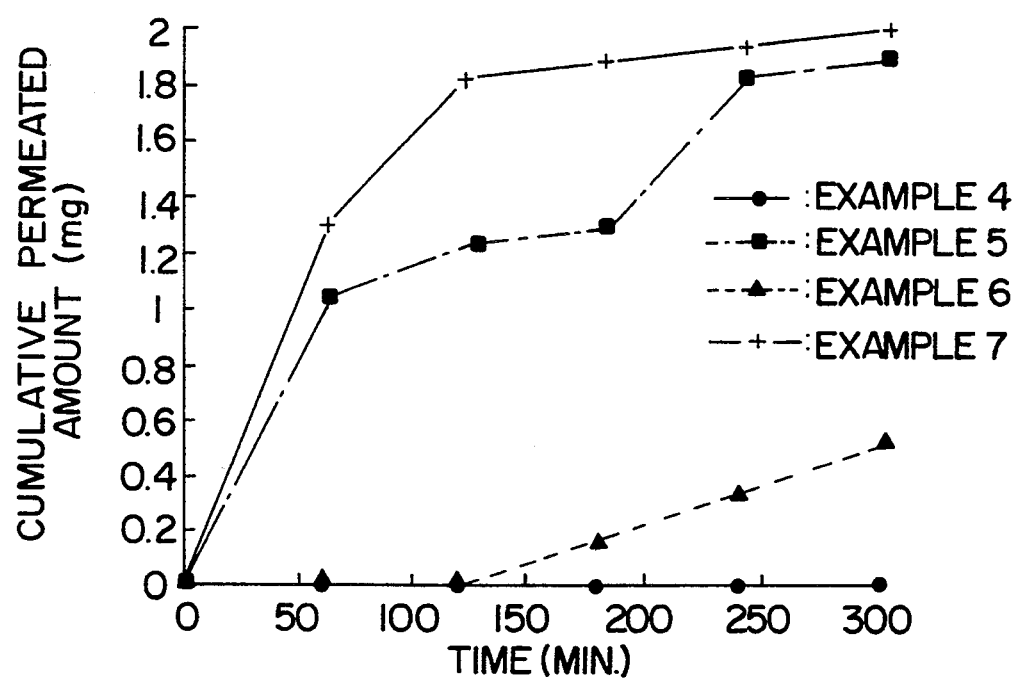

The cumulative permeated amounts of the chemicals are plotted in FIGS. 1 to 5.

The films formed from the copolymer of Examples 1 to 7 had much better effects for preventing permeation of the chemicals than the films formed from the copolymer of Comparative Example 1.

2. Film formability

On a clean film of polyethylene terephthalate (PET), a solution was coated with a doctor knife to a solid amount of 5 g/m² and dried at room temperature. All the solutions formed transparent dense films with gloss but no tackiness.

3. Brushing resistance

On the film formed on the PET film, a No. 3 abrasive piece was reciprocated 50 times under load of 200 g. Then, the surface condition of the film was observed. No irregularity was observed.

4. Removal of formed film

On the film formed on the PET film, a quantity of 2% aqueous ammonia or ethanol was dropped and easiness of film removal was observed.

All the films were swelled and peeled with aqueous ammonia after 2 minutes from dropping and completely removed with a cloth. All the films were dissolved in ethanol after 2 minutes from dropping and completely removed with a cloth.

What is claimed is:

1. A method of protecting the skin, which comprises applying to the skin a skin-protective amount of a composition which consists essentially of an acrylic copolymer consisting of
    (A) 40 to 85% by weight of an alkyl acrylate,
    (B) 5 to 50% by weight of an alkyl methacrylate, and
    (C) 10 to 30% by weight of a mono-ethylenically unsaturated monomer having a carboxyl group, and a medium.

2. The method according to claim 1, wherein the alkyl acrylate (A) is selected from the group consisting of ethylacrylate, propyl acrylate and butyl acrylate.

3. The method according to claim 1, wherein the alkyl methacrylate (B) is selected from the group consisting of methyl methacrylate and ethyl methacrylate.

4. The method according to claim 1, wherein the mono-ethylenically unsaturated monomer (C) is selected from the group consisting of acrylic acid, methacrylic acid, crotonic acid, itaconic acid, maleic acid, fumaric acid, half-esters of maleic acid and half-esters of fumaric acid.

5. The method according to claim 1, wherein the acrylic copolymer has a glass transition temperature of −10° C. to +50° C.

6. The method according to claim 1, wherein the acrylic copolymer has a weight average molecular weight of 30,000 to 1,500,000.

7. The method according to claim 1, wherein the medium is selected from the group consisting of ethanol, isopropanol, a mixture of water and ethanol and a mixture of water and isopropanol.

8. The method according to claim 1, wherein the composition is a solution of the copolymer and the medium.

9. The method according to claim 8, wherein a concentration of the copolymer in the medium is from 1 to 30% by weight.

* * * * *

UNITED STATES PATENT AND TRADEMARK OFFICE
CERTIFICATE OF CORRECTION

PATENT NO. : 5,346,977

DATED : September 13, 1994

INVENTOR(S) : Yoshio SASAKI; Izumi SAITOH

It is certified that error appears in the above-identified patent and that said Letters Patent is hereby corrected as shown below:

On the title page, item [75] Inventor's: last name should read --Sasaki--.

Signed and Sealed this

Sixth Day of June, 1995

Attest:

BRUCE LEHMAN

*Attesting Officer*    *Commissioner of Patents and Trademarks*